United States Patent
Kingsbury

[11] Patent Number: 5,142,228
[45] Date of Patent: Aug. 25, 1992

[54] METHOD FOR STATICALLY OR DYNAMICALLY MONITORING THE THICKNESS OF ELECTRICALLY-CONDUCTIVE COATINGS ON OPTICAL FIBERS

[75] Inventor: Paul I. Kingsbury, Elmira, N.Y.
[73] Assignee: Corning Incorporated, Corning, N.Y.
[21] Appl. No.: 670,354
[22] Filed: Mar. 14, 1991

Related U.S. Application Data

[63] Continuation of Ser. No. 342,285, Apr. 24, 1989, abandoned.

[51] Int. Cl.⁵ .............................................. G01B 7/10
[52] U.S. Cl. ................................... 324/230; 324/236; 324/653; 324/654; 427/10
[58] Field of Search .................. 324/226–231, 324/234, 236, 237, 238, 262, 240, 241, 207.16, 635, 662, 653, 654; 427/8–10, 163

[56] References Cited

U.S. PATENT DOCUMENTS

| | | | |
|---|---|---|---|
| 1,771,055 | 7/1930 | Pender | 427/10 X |
| 3,064,184 | 11/1962 | Watkiss | 324/230 |
| 3,679,968 | 7/1972 | Commercon et al. | 324/230 X |
| 4,567,437 | 1/1986 | Hubbard | 324/237 |
| 4,593,244 | 6/1986 | Summers et al. | 324/230 |
| 4,695,797 | 9/1987 | Deutsch et al. | 427/10 X |
| 4,803,428 | 2/1989 | Crostak | 324/230 |
| 4,825,158 | 4/1989 | Watabe et al. | 324/237 |
| 4,952,226 | 8/1990 | Frazee, Jr. et al. | 65/3.12 |

*Primary Examiner*—Kenneth A. Wieder
*Assistant Examiner*—Warren S. Edmonds
*Attorney, Agent, or Firm*—Stephen R. Christian; Kenneth McNeill Taylor

[57] ABSTRACT

Method and apparatus for non-destructively monitoring the thickness and uniformity of electrically conductive coatings (12) that have been deposited upon optical waveguide fibers (10). The monitoring may be performed while coated fiber (22) is at rest or while it is in motion. Physical contact with fiber (22) is not required. Monitoring is accomplished by feeding coated fibers (22) through an inductive coil (24) while simultaneously measuring an electrical value that is dependent upon the electrical resistance of conductive coating (10) then passing through inductive coil (24). The electrical value measured for a given section of coated fiber (22) becomes indicative of the coating thickness and uniformity of the coating about optical waveguide fiber (10) by correlating the electrical value measured with previously measured electrical values generated by coated fibers having coatings of known thicknesses and having no bald spots or other non-uniformities.

3 Claims, 3 Drawing Sheets

METHOD FOR STATICALLY OR DYNAMICALLY MONITORING THE THICKNESS OF ELECTRICALLY-CONDUCTIVE COATINGS ON OPTICAL FIBERS

This is a continuation of Ser. No. 342,285, Apr. 24, 1989, now abandoned.

BACKGROUND OF THE INVENTION

1. Field of the Invention

This invention relates to the field of monitoring particular characteristics of coatings and films that have been deposited upon optical fibers, and specifically to monitoring the thickness and uniformity of such coatings and films that are electrically conductive.

2. Description of the Prior Art

It is well known in the art that the deposition of certain thin films, or coatings, on bare optical glass fibers effectively reduces water corrosion and other chemically induced stress corrosion of the fibers. In addition, thin films and coatings are effective in reducing light, attenuation through the fiber attributable to the absorption of hydrogen into the fiber from the environment. Such films or coatings are often referred to as hermetic coatings.

It is also common in the art to apply an additional outer protective coating over a previously deposited hermetic coating. This is to ensure that the hermetic coating is not damaged or portions inadvertently removed while the optical fiber is being handled or while the optical fiber is in service.

Hermetic coatings can be, and often are, categorized according to whether a coating is made of: an electrically conductive material, e.g., a material made predominately of carbon or metal; a semi-conductive material, e.g., silicon carbide; or a non-electrically conductive material, e.g., an inorganic material or a ceramic material If a particular hermetic coating is electrically conductive, or semi-conductive, the coating will consequently have a measurable linear electrical resistivity. The resistivity may be expressed in terms of ohms per centimeter, or other units that may be convenient.

It is a known concept in the art that the magnitude of the electrical resistivity is influenced by such factors as the thickness and/or the uniformity of the coating over a given length of the coated fiber. Subsequently it is known that as coating thickness increases, electrical resistance decreases. It is also known that a non-uniformity such as a bare section of an otherwise properly coated fiber would cause an increase in electrical resistance. Another example of coating uniformity affecting electrical resistance is a coating consisting of a mixture of a conductive material and a non-conductive material, wherein the coating thickness is acceptable, but the differing materials are improperly proportioned.

As previously known, and conceptually representative of similar methods for measuring the electrical resistivity of a conductive hermetic coating utilizes a pair of suitable contacts which are connected to a standard commercially available ohm-meter. The contacts are positioned at a predetermined distance from each other along the axis of the coated fiber to be measured. A measurement of the resistance between the points of contact is then taken and the value noted. If the hermetically coated fiber to be measured has an additional outer protective coating, a pair of razor blades can effectively be used as contact points. The razor blades are convenient for cutting through the outer protective coating while also providing electrical contact with the conductive hermetic coating below. An apparatus for carrying out this previously known method is illustrated in FIG. 1, wherein razor blades 70 and 72 are separated at a predetermined length by being fixed at opposite ends of an insulating block 74 and are respectively connected to ohm-meter means 78. Coated fiber to be measured 76, and razor blades 70 and 72, are then brought into contact with each other and the corresponding value of linear resistance is read from ohm-meter means 78.

After measuring the electrical resistance of a known length of a given coating, the thickness of a particular coating can then be empirically correlated with the measured resistance. This correlation is achieved by measuring the electrical resistance of a previously identified segment of a given coated optical fiber, and then measuring the actual thickness of the hermetic coating by measuring a cross-sectional sampling of that particular segment of coated fiber by electron microscopy, or by other methods. Thereafter, the correlation is carried out over a number of various coating thicknesses for a particular coating in order to set an acceptable range of resistivity that will indicate that coating thickness is meeting previously set production or quality assurance standards.

Correlation of coating uniformity can be carried out much the same way, except that a chemical analysis or a magnified visual inspection of the coating would be substituted for the measuring of coating thickness as set forth above.

A disadvantage with previously known methods of monitoring conductive hermetic coatings by electrical contact is that a portion of any protective coating present on the fiber must either be penetrated, mechanically removed, or chemically removed in order for electrical contact to be made with the hermetic coating underneath.

Another disadvantage with previously known methods of monitoring conductive hermetic coatings by electrical contact is that the section of hermetically coated optical fiber that is measured is usually rendered unusable by the physical contact between the electrical contact points and the hermetic coating. This is due to the fact that many optical fibers are very fragile and a nick or a scratch to or through the hermetic coating could produce a flaw in the form of a stress concentration in the fiber below. Thus, measuring the resistance of coatings at any place along the fiber other than end portions by previously known methods, necessitates undesirable splicing of the fiber to remove areas where flaws may have been created.

A further disadvantage with currently known methods of monitoring conductive coating thicknesses by electrical contact is that the electrical resistivity measurements can only be made on a time consuming static basis and not on a continuous/dynamic basis. In other words, the optical fiber being monitored must be stationary, or at least be moving very slowly, before a sample of that fiber may be removed and measurements be performed thereon. This precludes monitoring the thickness of the optical fiber while it is in motion such as on a high-speed production line. Therefore, there remains a need in the art for a quick and a non-destructive method for either statically or continuously monitoring coating thickness and/or coating uniformity without impeding the motion of the coated fiber.

SUMMARY OF THE INVENTION

It is an object of this invention to provide for the non-destructive static monitoring of coating characteristics such as the thickness and/or uniformity of electrically conductive hermetic coatings, or films, that have been deposited upon optical fibers.

Another object of this invention is to provide for the non-destructive dynamic monitoring of coating characteristics such as the thickness and/or uniformity of electrically conductive hermetic coatings, or films, that have been deposited upon optical fibers. i.e., the continuous monitoring of a coated fiber while the coated fiber is in motion, for example, when the coated fiber is being manufactured in a production line or when a coated fiber is being transferred from one reel to another.

A further object of this invention is to provide for the static or dynamic monitoring of the thickness and/or uniformity of electrically conductive hermetic coatings, or films, that have been deposited upon optical fibers, wherein a second essentially non-conductive protective coating has been placed over the hermetic coating.

A still further object of this invention is to provide for either the static or dynamic monitoring of the thickness of electrically conductive hermetic coatings, or films, that have been deposited upon optical fibers, including fibers having a second protective coating placed over the hermetic coating, whereby the monitoring is performed quickly, and is performed without physically contacting the coatings or the fiber, and is therefore non-destructive.

The above and other objectives are accomplished by feeding coated fibers through an inductive coil while simultaneously measuring an electrical value that is dependent upon the electrical resistivity of the conductive coating then positioned within the inductive coil. The electrical value measured for a given section of coated fiber is then correlated with the coating thickness and/or coating uniformity of that section, by comparing the value measured with previously measured electrical values generated by coatings of known thicknesses and/or uniformities.

The foregoing and other features and advantages of the present invention will become more apparent from the following description, drawings, and appended claims.

DETAILED DESCRIPTION OF THE INVENTION

Figure 2A:
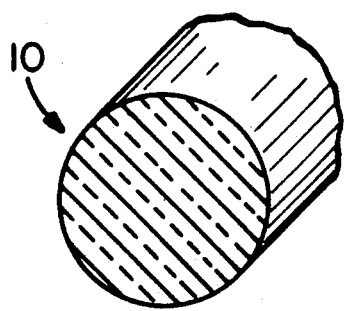
FIG. 2A is an oblique view of an uncoated optical fiber.
Figure 2B:
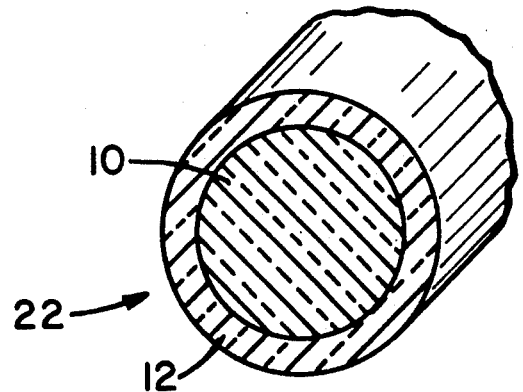
FIG. 2B is an oblique view of an optical fiber having a hermetic coating.
Figure 2C:
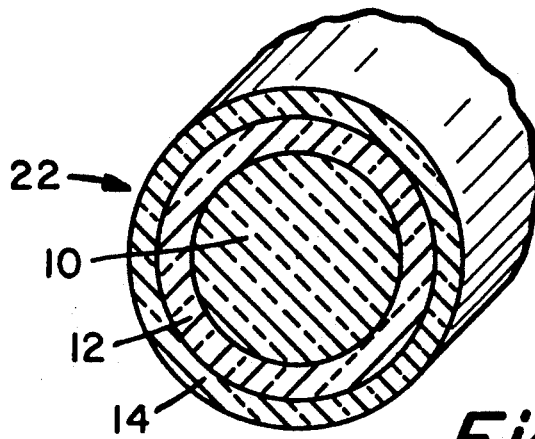
FIG. 2C is an oblique view of an optical fiber having a hermetic coating and an outer protective coating.

Referring now to the drawings, FIGS. 2A, 2B, and 2C show sections of representative optical fibers being shown in various states.

FIG. 2A shows an uncoated bare optical fiber 10. Fiber 10 may be made of any essentially non-electrically conductive material or materials in which a thin film or hermetic coating is to be disposed thereon. In addition fiber 10 may employ any design, i.e., a core surrounded by cladding (not shown) or a core having a material dispersed within (not shown).

FIG. 2B shows a fiber having electrically conductive coating 12 disposed upon fiber 10. Coating 12 is preferably hermetic. Hermetic coating 12 may be applied to fiber 10 by any previously chosen process, as the present invention is not restricted by the process used to apply the coating. Hermetic coating 12 is sometimes referred to as a thin-film. The reason being that these films, or coatings, typically have thicknesses of less than 3000 Angstroms ($3000 \times 10^{-8}$ centimeters). Preferably, the hermetic coating thickness is between 300 and 1500 Angstroms.

With respect to the present invention, hermetic coating 12, or any coating that is to be monitored, must be of a conductive or semi-conductive material, or in the alternative, be made of a combination of materials in which at least one material is electrically conductive and will therefore have a measurable linear resistance that depends upon the thickness or uniformity of that particular coating.

FIG. 2C shows fiber 10 having hermetic coating 12 being covered by outer most protective coating 14. Typically, protective coating 14 comprises acrylate or silicone compositions. Protective coating 14 provides abrasive protection to hermetic coating 12, while also providing additional protection to the fiber below. Protective coating 14 may be applied by any appropriate process. The presence or absence of protective coating 14 will not affect coating monitoring by the present invention provided that protective coating 14 is made of an electrically non-conductive material. Therefore protective coating 14 should be made of a non-conductive material if hermetic coating 12 is to be easily monitored. For convenience, reference number 22 shall be used herein to designate a coated fiber that has been chosen to be monitored, and said fiber may or may not include protective coating 14.

Figure 3A:
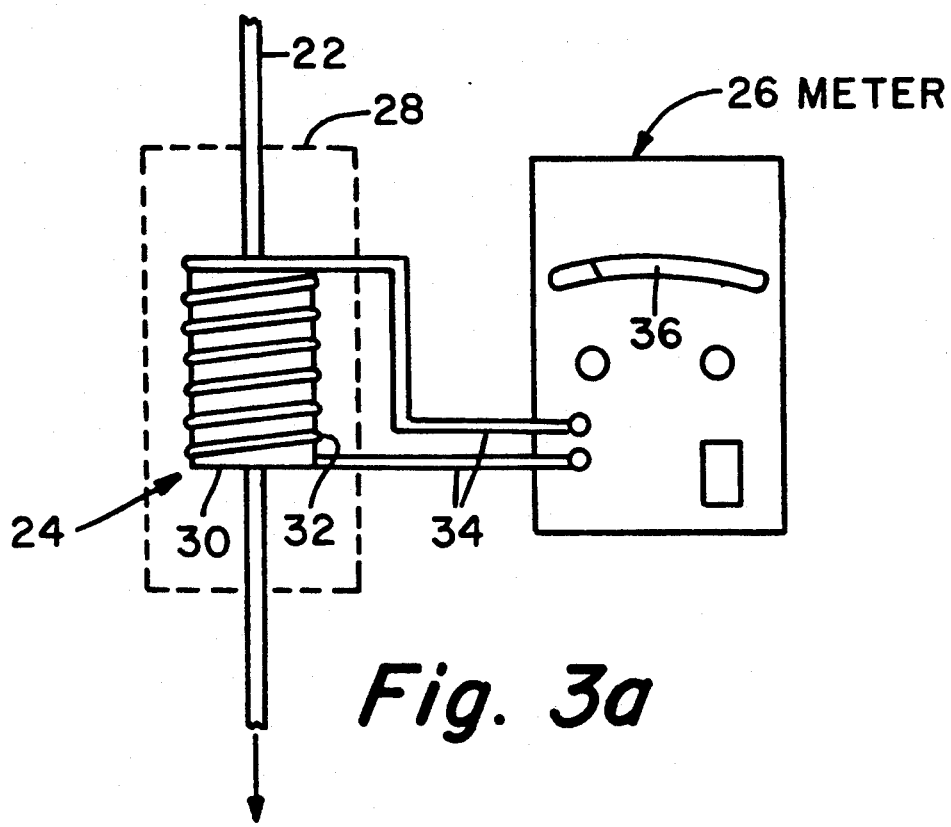
FIG. 3A is a view of an embodiment for dynamically monitoring hermetically coated fiber by the herein disclosed invention.

An embodiment of the present invention is shown in FIG. 3A. This particular embodiment is illustrative of an apparatus for either intermittently or continuously monitoring coating characteristics of coated fiber 22 by herein disclosed methods. Apparatus 20 includes inductive coil 24, being electrically connected by leads 34 to Q-meter means 26. Q-meter means 26 is shown as incorporating an analogue or digital display meter means 36 for displaying a measured electrical value (Q) in response to the energizing of inductive coil 24. Inductive coil 24 is surrounded by an optional electrical interference shielding 28 which has been illustrated with a dotted line. The exact configuration of shielding 28 will depend upon restrictions present at the installation site and hence the size and extent of shielding 28 will vary accordingly to the intstallation site. Shielding 28 may be of any suitable electrically conductive material such as steel in sheet or mesh form.

A discussion of the theory and operation of the disclosed monitoring process and apparatus is set forth below, followed by discussion of the construction of an optimized inductive coil.

The Q of a reactive circuit element, i.e., a circuit having an inductor (L) or a capacitor (C), is defined as the ratio of the element's reactance (X) to its series resistance:

$$Q = 2\pi \frac{\text{Energy stored per cylce}}{\text{Energy lost per cycle}}$$

For an inductor this is given by:

$$Q = \frac{X_L}{R} = \frac{\omega L}{R} = \frac{2\pi f L}{R}$$

where L is the inductance, R is the resistance associated with the inductor, $\omega$ is angular velocity and f is the corresponding frequency. In a high-Q circuit, where resistive losses are small, the value of Q can typically range from 100-900.

Inserted electrical losses, such as those resulting from a carbon-coated optical fiber being passed through a high-Q inductive coil, can be detected easily by noting the subsequent change in the value of Q of the circuit. This is attributable to the linear dependency of Q upon the logarithmic value of the resistivity of the conductive coating deposited upon the fiber being monitored. Therefore fluctuations in the magnitude of Q indicate changes in the resistivity of the coating being monitored. Any such changes in the resistivity of the coating are due to variations occuring in the thickness and/or uniformity of the coating being monitored. Hence, as coating thickness and/or coating uniformity increases, the magnitude of Q will decrease, and conversely, as coating thickness and/or coating uniformity decreases, the magnitude of Q will increase.

Figure 1:
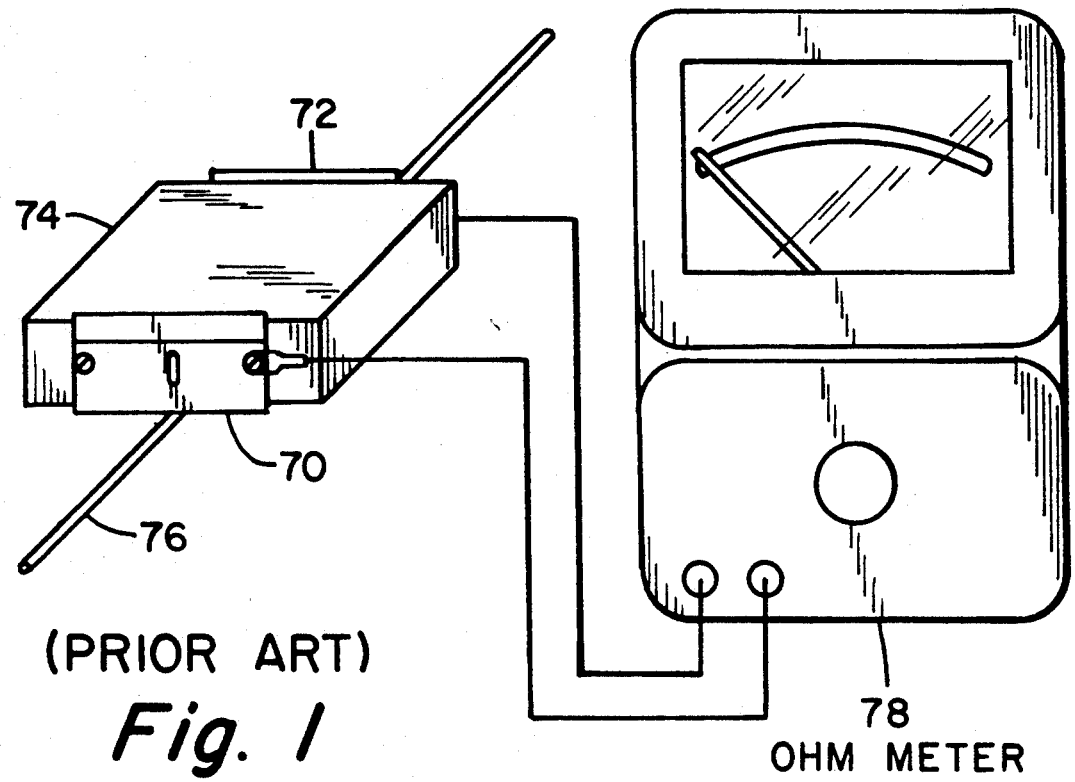
FIG. 1 is a view, partly in perspective, of a prior art arrangement for measuring the electrical resistivity of electrically conductive coatings on optical fibers.

The above relationships are verifiable mathematically and also by measuring Q for coatings of differing thicknesses and/or uniformities and then measuring the resistivity by priorly known techniques and apparatuses such as the one shown in FIG. 1.

Figure 3B:
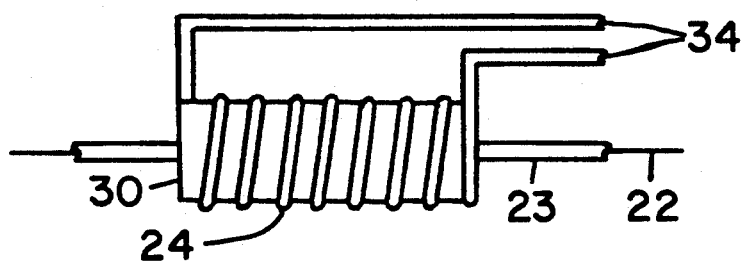
FIG. 3B is a view of an embodiment for statically monitoring hermetically coated fiber by the herein disclosed invention.
Figure 3C:
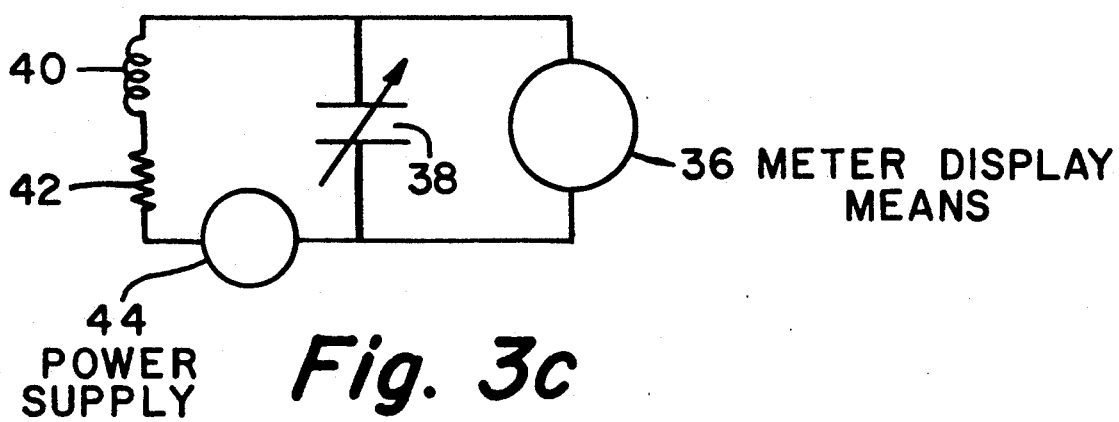
FIG. 3C is a diagrammatic view of a simplified electrical circuit for demonstrating the operation of a portion of the herein disclosed invention.

The operation of a Q-meter means per se is based on the well known fact that the voltage across either reactive element (L or C) in a series resonant circuit is Q multiplied by the applied voltage when the circuit configuration is that shown in FIG. 3C.

Although Q provides a straightforward value for measurement, electrical measurements are not restricted to Q alone. The measurement of any electrical value that characterizes a reactive circuit can be used as an indicator of coating characteristics in lieu of Q. Examples of such electrical values include impedance, reactance, phase shift, phase angle, and frequency shift.

Consequently, FIG. 3C is a simplified diagram of Q-meter means 26 (shown in FIG. 3A.), wherein meter display means 36 is connected to inductor 24 (schematically represented by inductive element 40 and associated series resistive element 42). Meter display means 36 is additionally connected to power source 44. Variable capacitor 38 is included in the Q-meter means circuit for tuning purposes. And it should be understood that the diagram of FIG. 3C is for illustrative purposes only, as there are other circuits known within the art for accomplishing Q-meter means.

Q-meters having appropriate power sources, variable capacitors, and meters for displaying Q are commercially available. A Boonton Q-meter, Model 260-A, manufactured by Boonton Radio Corp., Boonton, N.J. was found to be adequate for practicing the invention. However, Hewlett-Packard Inc., Palo Alto, Calif., currently markets a Q-meter designated as Model 4342A, which may be more suitable for practicing the present invention due to it having enhanced bandwidth characteristics.

Bandwidth becomes a concern when the coated fiber to be monitored is in motion, such as in high speed reel-to-reel monitoring, or when monitoring coated fiber while it is on-line in a high-speed fiber drawing apparatus. Therefore the bandwidth of the Q-meter being used should be of a value that will enable the Q-meter to resolve resistivity variations over desired segmented lengths of coated fiber. For example, if the speed of the coated fiber to be monitored is the preferred 6.5 meters per second, then the value of Q must be taken every 1/100 second in order to resolve variations in resistivity over 6.5 centimeter segments of the coated fiber. Thus, a Q-meter having a bandwidth greater than 100 hertz would be desired for this fiber speed.

In light of the preceding, it is feasible to design and construct a Q-meter having features and characteristics that have been optimized for practicing the herein disclosed method of monitoring specific types of coated fibers, at various speeds including the preferred fiber speed, while also providing for the resolution of predetermined segment lengths.

Returning to FIG. 3A, it is recommended that prior to monitoring coated fiber 22, inductive coil 24 should first be energized and the coil tuned in an unloaded state. An unloaded state is defined as an inductive coil not having a fiber or other object in or proximate to the coil that would unduly influence Q. Tuning is accomplished by energizing the unloaded inductive coil at a preselected frequency and then adjusting a variable capacitor usually included within Q-meter means 26, in order to find the resonant frequency which will also yield the highest value of Q for the unloaded inductive coil 24. Tuning inductive coil 24 before monitoring coated fiber 22, ensures that the coil will optimally respond to variations of the coating characteristics to be monitored.

After tuning the inductive coil, all monitoring is performed while the inductive coil is energized at the frequency which provided the highest Q during the tuning procedure. A helpful simplified expression for estimating resonant frequency of a Q meter circuit is:

$$f = [2\pi(LC)^{0.5}]^{-1}).$$

Resonant frequencies for practicing the herein disclosed invention typically range from 1 to 10 MHz).

To carry out the monitoring process, coated fiber 22 is then fed through inductive coil 24 by any appropriate means (not shown) while the Q of inductive coil 24 is measured and displayed by Q-meter 26 and meter means 36 respectively. The Q of the coil is reduced due to loading of inductive coil 24 by hermetic coating 12 of coated fiber 22. Fluctuations of Q indicate changes in a coating characteristic of the coating then located within inductive coil 24. The value of Q need not be displayed on meter means 36. For example, the value of Q can be recorded on strip charts or stored in an electronic or other medium to be examined later. Having the values of Q fixed in a tangible form would be especially useful for quality control, production control, or for verification purposes.

Again referencing FIG. 3A, the general design criteria of inductive coil 24 will now be addressed. The optimal inductive coil will be capable of large values of Q in order to maximize the sensitivity of the inductive coil to coating characteristics, and will have overall dimensions that minimize variations in Q not attributable to changes in coating characteristics.

A relatively large coil diameter is desirable in order to minimize changes in Q due to lateral displacements of coated fiber 22 within inductive coil 24. This is because the Q of the coil may be somewhat reduced as the coated fiber moves away from the longitudinal centerline of the coil and moves toward windings 32 of the coil.

The diameter of inductive coil 24 is likely to be limited by the presence of structures near the inductive coil. Therefore some down sizing from an optimized diameter may be required, especially if the interfering structure is electrically conductive. Such an interfering structure will decrease the unloaded value of Q, and hence decrease the sensitivity of the inductive coil.

Optional electrical interference shielding 28 is a way to reduce undesired electrical interference with Q, e.g., people and structures near the inductive coil. However, the shielding itself is likely to be electrically conductive and will consequently have a negative effect on Q. Therefore shielding 28 should be employed only as necessary and to such an extent as to reduce unacceptable interference without unduly limiting the monitoring sensitivity of the coil.

Core 30 of inductive coil 24 is a means for supporting windings 32. Core 30 is preferably non-electrically conductive and non-magnetic. Core 30 is preferably hollow in order for coated fiber 22 to pass freely through the common longitudinal axis of windings 32. If the monitoring is to be performed continuously on a moving coated fiber, the internal diameter of hollow core 30 should be large enough to allow coated fiber 22 to laterally deviate from the longitudinal central axis of the core without brushing against the interior of the core.

If previously cut segments of fiber are to be monitored on a static basis, it is recommended that means for axially centering the segment within the inductive coil be employed to maintain coil sensitivity. This is especially important if inductive coil 24 is to be positioned horizontally or at an angle. FIG. 3B provides an illustration of such an embodiment of inductive coil 24 being positioned horizontally and having a fiber support means 23 axially positioned and supported within the inductive coil by appropriate non-electrically conductive support means. A horizontal orientation is convenient for mounting the inductive coil upon a working surface such as a bench or table. Previously cut segments of coated fiber 22 can easily be inserted into fiber support means 23 and subsequently be removed after the static monitoring process has been performed. A glass pippette was found to be particularly suitable for use as a fiber support means 23.

It is recommended that fiber support means 23 be used primarily for bench monitoring previously cut short segments of fiber, as it is generally desirable to avoid physically contacting coated fibers anymore than what is necessary.

The general design criteria for high Q coils have been studied over many years, particularly in the field of radio. F.E. Terman in *Electronic and Radio Engineering*, fourth edition, published by McGraw-Hill (1955), listed the principal losses in an inductive coil as skin effect and proximity of the windings effect and distributed capacitance and eddy currents in neighboring objects.

Copper wire is typically used to form wire windings 32. Although copper wire has significant skin effects at 1 Megahertz, copper windings were found to perform adequately in the present invention. Forming wire windings 32 with Litz wire would enhance the sensitivity of inductive coil 24.

The effect of the proximity of one winding to another is addressed by K.R. Sturley, in *Radio Receiver Design*, third edition, published by Chapman and Hall (1965), and is also addressed by Terman, supra. Sturly suggested that the optimum wire diameter for windings is 0.7 times the pitch of the winding. Pitch is defined as the center-to-center distance between adjacent windings. For example, if there were 21 windings, or turns, of wire evenly spaced about a core 9 centimeters long, the pitch would be 0.43 centimeters/turn. Terman suggests that the optimum wire diameter for windings is 0.5 to 0.75 times the pitch of the winding. A 2.8 millimeter diameter wire, not including insulation, was used with a pitch of 4.5 millimeters/turn to result in a wire diameter to pitch ratio of 0.63—which proved to be adequate to practice the invention while also falling within the recommended ratios.

As discussed earlier, Eddy currents can be induced in conductive objects located near the inductive coil and thereby negatively influence Q. Consideration should be given to the location of the inductive coil with respect to conductive structural members and to moving objects as well as shielding to minimize undesired variances in the Q of the inductive coil.

Terman recommends that the optimum length to diameter ratio of the inductive coil is approximately 0.96. Sturly recommends that an optimum length to diameter ratio ranges from 0.3 to 0.45. However, an inductive coil having a length to diameter ratio of 0.86 was found to be suitable.

There are several mathematical methods known within the art for estimating Q and inductance of a given inductive coil as well as other suitable values that may be used in place of Q that may be helpful in designing an optimal embodiment of an apparatus for practicing this invention in a given application. These methods are readily available in reference materials that are familiar to those in the art.

The following is a summary of the configuration of an exemplary embodiment of the inductive coil as illustrated in FIG. 3A follows.

Outside diameter of hollow Core 30—10 centimeters
Length of hollow core 30—9 centimeters
Overall diameter of coil 24 (to center of windings) —10.5 centimeters
Overall length of coil 24—9 centimeters
Number of windings 32 (turns of wire) —21 turns
Wire winding 32 diameter (not including insulation) —2.8 millimeters
Winding 32 material—stranded copper wire
Winding pitch—4.5 millimeters/turn
Winding diameter to pitch ratio—.63

Coil length to diameter ratio—.86
As a result of tuning, coil was energized
at a frequency of 4.2 MHZ while monitoring.

The configuration above is merely exemplary, and the coil configuration can be further optimized to suit various applications. Additionally the recommendations set forth in the reference materials cited above need not be adhered to strictly, but are offered only as guidelines.

Details of electrical circuits as actually used within Q-meter 26 itself, have not been included herein due to Q-meters being available commercially and due to there being numerous circuits available to those within the art who may wish to construct an optimized version of Q-meter 26.

Figure 4:
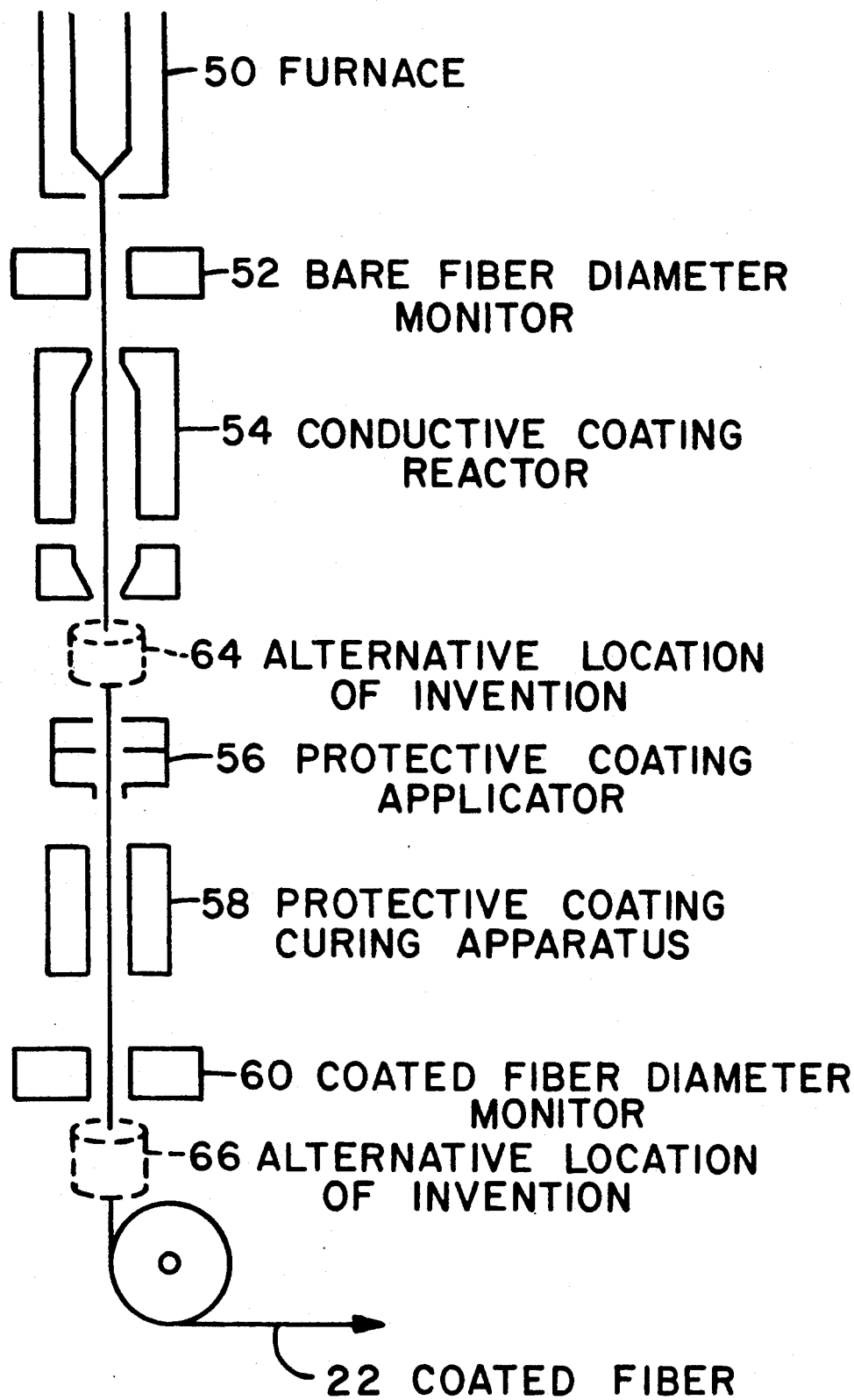
FIG. 4 is a diagrammatic view of an optical fiber drawing and coating line with exemplary placements of an appropriate embodiment of the herein disclosed invention.

A schematic of a typical optical fiber drawing line is shown in FIG. 4. Furnace means 50 is used to heat the optical fiber material to temperatures great enough to enable bare fiber 10 to be drawn therefrom. Bare fiber diameter monitor means 52 is used to ensure that bare fiber 10 is being drawn to a proper outside diameter. Reactor means 54 is for placing electrically conductive coating 12, such as carbon, upon bare fiber 10. Protective coating applicator means 56 is used to place subsequent coating 14, such as a polymer material, upon fiber 10 which already has conductive coating 12 thereon. Curing means 58 is used to cure protective coating 14. Coated fiber diameter monitor means 60 is used to ensure that now finally coated fiber 22 is of a proper outside diameter. Coated fiber 22 is then passed onto a take up spool or reel.

An embodiment of inductive coil 24 may be installed any where along the drawing line subsequent to reactor 54. For example, an embodiment of inductive coil 24 could be installed at position 64 or position 66 as shown in FIG. 4. Alternatively, a number of inductive coils could be positioned in the drawing line for redundant fiber monitoring, or inductive coils could be installed that are designed to perform specific tasks. For instance, a coil designed for installation within a feedback control system to regulate fiber production could be used concurrently with a inductive coil specifically designed for quality assurance purposes.

Lastly, as mentioned earlier in the present specification, the present invention can be used to monitor coating characteristics off-line for quality assurance purposes.

Although the invention has been shown and described with respect to detailed embodiments thereof, it will be understood by those skilled in the art that various changes in the form and detail thereof may be made without departing from the spirit and scope of this invention.

I claim:
1. A method for statically monitoring the thickness of a carbon coating less than 1500 Angstroms thick on an optical fiber having an outside diameter less than 300 microns comprising:
   a) energizing an inductive coil with an electrical power source having means for influencing the power output;
   b) measuring an electrical parameter of the inductive coil while the inductive coil is in an unloaded state;
   c) tuning the inductive coil while the inductive coil is in an unloaded state;
   d) positioning a segment of the coated fiber axially within the inductive coil after tuning the inductive coil, in an unloaded state;
   e) measuring the electrical parameter of the coil with the selected segment of the coated fiber within the inductive coil; and
   f) comparing the measured electrical parameter with previously measured electrical parameters generated by like coated optical fibers having known coating thicknesses.

2. A method for dynamically monitoring the thickness of a carbon coating less than 1500 Angstroms on a moving optical fiber having an outside diameter less than 300 microns comprising:
   a) energizing an inductive coil with an electrical power source having means for influencing the power output;
   b) measuring an electrical parameter of the inductive coil while the inductive coil is in an unloaded state;
   c) tuning the inductive coil in order to optimize the magnitude of the electrical parameter while the inductive coil is in an unloaded state;
   d) continuously feeding the optical fiber axially through the inductive coil;
   e) continuously measuring the electrical parameter as the optical fiber is being fed through the inductive coil; and
   f) comparing the measured electrical parameter with previously measured electrical parameters generated by like coated optical fibers having known coating thicknesses.

3. A method for monitoring the thickness of a carbon coating less than 1500 Angstroms on an optical fiber having an outside diameter less than 300 microns comprising:
   a) energizing an inductive coil with an electrical power source;
   b) positioning the optical fiber axially within the inductive coil; and
   c) monitoring an electrical parameter of the energized inductive coil which varies as a function of the thickness of the carbon coating.

* * * * *